United States Patent
von der Osten et al.

[11] 4,427,440
[45] Jan. 24, 1984

[54] HERBICIDES BASED ON CYCLOHEXANE-1,3-DIONE DERIVATIVES AND 3,6-DICHLORO-2-PICOLINIC ACID DERIVATIVES

[75] Inventors: Eckhart von der Osten, Speyer, Fed. Rep. of Germany; James F. Stewart, Cambridge; John M. Bennett, Willowdale, both of Canada

[73] Assignee: BASF Aktiengesellschaft, Fed. Rep. of Germany

[21] Appl. No.: 294,238

[22] Filed: Aug. 19, 1981

[30] Foreign Application Priority Data

Aug. 27, 1980 [DE] Fed. Rep. of Germany ....... 3032259

[51] Int. Cl.$^3$ ............................................. A01N 43/40
[52] U.S. Cl. ........................................... 71/94; 71/98; 71/103
[58] Field of Search ..................... 71/94, 98

[56] References Cited

FOREIGN PATENT DOCUMENTS 1228848 11/1966 Fed. Rep. of Germany .
2439104  3/1975 Fed. Rep. of Germany .
2822304 11/1978 Fed. Rep. of Germany .
1481389  7/1977 United Kingdom .

OTHER PUBLICATIONS

Herbicide Handbook of the Weed Science Society of America, 4th Ed. (1979), pp. 161–163.

*Primary Examiner*—Catherine L. Mills
*Attorney, Agent, or Firm*—Keil & Witherspoon

[57] ABSTRACT

Herbicides containing a mixture of a cyclohexane-1,3-dione derivative of the formula

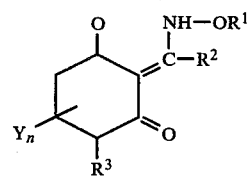

where $R^1$, $R^2$, $R^3$, Y and n have the meanings given in the description, and a 3,6-dichloro-2-picolinic acid derivative of the formula

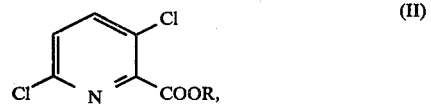

(II)

where R has the meaning given in the description. These herbicide mixtures display a synergistic action, especially on grassy plants.

2 Claims, No Drawings

HERBICIDES BASED ON CYCLOHEXANE-1,3-DIONE DERIVATIVES AND 3,6-DICHLORO-2-PICOLINIC ACID DERIVATIVES

The present invention relates to herbicides containing mixtures of cyclohexane-1,3-dione derivatives and 3,6-dichloro-2-picolinic acid derivatives, and to methods of controlling undesired plant growth by means of these herbicides.

Cyclohexane-1,3-dione derivatives are known herbicides, whose activity is particularly directed against grass weeds and grassy crop plants. At the same time, they are tolerated very well by broad-leaved crop plants (German Published Application DAS No. 2,439,104 and German Laid-Open Application DOS No. 2,822,304).

3,6-Dichloro-2-picolinic acid and its salts and esters are also known herbicides (German Published Application DAS No. 1,228,848) having an activity which is preferentially directed against broad-leaved plants but not against plants of the Cruciferae family. In contrast, they are not very effective on grasses (Herbicide Handbook of the Weed Science Society of America, 4th edition, 1979, page 161).

We have found that herbicides containing a mixture of a cyclohexane-1,3-dione derivative of the formula I

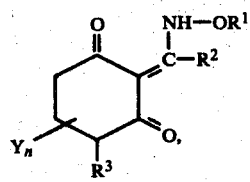

where $R^1$ is straight-chain or branched alkyl of 1 to 4 carbon atoms, which can be substituted by alkoxy, alkylthio of up to 4 carbon atoms or alkoxycarbonyl of up to 5 carbon atoms, or straight-chain or branched alkenyl or alkynyl of up to 4 carbon atoms or benzyl, $R^2$ is hydrogen or straight-chain or branched alkyl of 1 to 4 carbon atoms, $R^3$ is hydrogen or alkoxycarbonyl of 2 to 5 carbon atoms, n is 0, 1, 2 or 3 and, if n is 1, 2 or 3, Y is straight-chain or branched alkyl of 1 to 4 carbon atoms, alkoxycarbonyl of 2 to 5 carbon atoms, halogen, cyano or phenyl which is unsubstituted or substituted by halogen, methyl or methoxy, or, if n is 1, Y is the radical $R^4S(O)_mX-$, where $R^4$ is alkyl of up to 4 carbon atoms, unsubstituted phenyl or phenyl or benzyl each of which is substituted by halogen or alkyl or alkoxy of up to 4 carbon atoms, X is straight-chain or branched alkylene of up to 4 carbon atoms and m is 0, 1 or 2, or of a metal salt, an unsubstituted or substituted ammonium salt or a hydrate of the above cyclohexane-1,3-dione derivative, and a 3,6-dichloro-2-picolinic acid derivative of the formula II

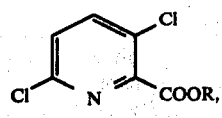

where R is hydrogen or straight-chain or branched alkyl of 1 to 4 carbon atoms, or a metal salt or unsubstituted or substituted ammonium salt of the acid, are more effective than herbicides containing only a cyclohexane-1,3-dione derivative of the formula I or a 3,6-dichloro-2-picolinic acid derivative of the formula II, and display a synergistic action, especially on grassy plants.

Examples of suitable components of the formula I in the mixture are cyclohexane-1,3-dione derivatives where $R^1$ is straight-chain or branched alkyl of 1 to 4 carbon atoms, which can be substituted by alkoxy, alkylthio or alkoxycarbonyl of up to 4 carbon atoms, such as methyl, ethyl, n-propyl, i-propyl, n-butyl, methoxymethyl, methoxethyl, butoxymethyl, ethoxycarbonylmethyl or methylthiomethyl, or straight-chain or branched alkenyl or alkynyl of up to 4 carbon atoms, such as allyl or propargyl, or benzyl, $R^2$ is hydrogen or straight-chain or branched alkyl of 1 to 4 carbon atoms, such as methyl, ethyl, n-propyl or n-butyl, $R^3$ is hydrogen or alkoxycarbonyl of 2 to 5 carbon atoms, such as methoxycarbonyl or ethoxycarbonyl, and Y is straight-chain or branched alkyl of 1 to 4 carbon atoms, such as methyl, ethyl, n-propyl, i-propyl, i-butyl or n-butyl, especially methyl, or alkoxycarbonyl of 2 to 5 carbon atoms, such as methoxycarbonyl or ethoxycarbonyl, or halogen, such as bromine, or cyano or phenyl which is unsubstituted or substituted by halogen, methyl or methoxy, such as 3-chlorophenyl, 4-methylphenyl, 4-chlorophenyl or 4-methoxyphenyl. If Y has these meanings, n is 1, 2 or 3, and the substituents Y can be identical or different if n is 2 or 3. If n is 1, Y can also be $R^4S(O)_mX-$, and is preferably in the 5-position on the cyclohexane-1,3-dione ring. $R^4$ is alkyl of 1 to 4 carbon atoms, such as methyl, ethyl, n-propyl, i-propyl or n-butyl, or is unsubstituted phenyl or phenyl or benzyl each of which is substituted by halogen or alkyl or alkoxy of up to 4 carbon atoms, such as 4-chlorophenyl, 2-methylphenyl, 3-methylphenyl, 4-methylphenyl, 2,5-dimethylphenyl, 2,4-dichlorophenyl or 4-methoxyphenyl, X is an alkylene group of up to 4 carbon atoms, such as the methylene, ethylene, methylethylene or ethylmethylene group, and m is 0, 1 or 2.

The compounds of the formula II can also be used in the form of metal salts, unsubstituted or substituted ammonium salts or hydrates, for example in the form of manganese, copper, zinc, cobalt, iron or silver salts, alkali metal or alkaline earth metal salts, e.g. sodium, potassium, calcium or barium salts, or unsubstituted or substituted ammonium salts, such as tetrabutylammonium, trimethylbutylammonium or dimethyl-benzylhexadecylammonium salts.

Preferred components of the formula I in the mixture are those where $R^1$ is ethyl or allyl, $R^2$ is alkyl of 2 or 3 carbon atoms, $R^3$ is hydrogen or methoxycarbonyl, Y is methyl and n is 1 or 2, or those where $R^1$, $R^2$ and $R^3$ have the above preferred meanings and Y is $R^4S(O)_mX-$, where $R^4$ is alkyl of 1 to 3 carbon atoms, unsubstituted phenyl or phenyl which is substituted by chlorine, methyl or methoxy, X is an alkylene group of 1 to 3 carbon atoms and m is 0 or 1, and n is 1.

2-(1-Ethoxyaminobutylidene)-5-(2-ethylthiopropyl)-cyclohexane-1,3-dione and 2-(1-allyloxyaminobutylidene)-5,5-dimethyl-4-methoxycarbonyl-cyclohexane-1,3-dione and the metal salts, especially the alkali metal salts, of the latter are particularly preferred.

Suitable components of the formula II in the mixture are 3,6-dichloro-2-picolinic acid and its salts or esters, for example lower alkyl esters or salts with metals, such as copper, iron, zinc, cobalt or nickel, alkali metals or kaline earth metals, e.g. sodium, potassium, lithium, magnesium or calcium, or the ammonium salt or substituted ammonium salts, such as alkylammonium or hydroxyalkylammonium salts, e.g. the methylammonium, dimethylammonium, trimethylammonium, ethylammonium, triethylammonium, hydroxyethylammonium, 3-hydroxypropyl-ammonium or bis-(2-hydroxypropyl)ammonium salt. Alkyl of 1 to 4 carbon atoms in the alkyl esters is preferably methyl.

The weight ratio of cyclohexane-1,3-dione derivative of the formula I to 3,6-dichloro-2-picolinic acid derivative of the formula II in the mixture can vary within a wide range. This ratio depends, in particular, on the spectrum of broad-leaved and grassy weeds to be controlled, on the development stage of the plants to be controlled, and on whether the herbicides are to be used selectively on herbaceous crop plants, on areas populated by trees or shrubs or for total control of vegetation, and is from 1:0.06 to 1:5, preferably from 1:0.06 to 1:3 and especially from 1:0.25 to 1:3.

The amount of active ingredient mixture applied in the herbicidal agents according to the invention depends on the composition of the stand, the development stage of the plants and the climatic conditions prevailing where the agents are to be used. Generally, the application rates are from 0.1 to 5 kg of active ingredient mixture per hectare and treatment.

Crops in which the herbicidal agents according to the invention may be used are essentially those broadleaved crops in which active ingredient B, at the requisite rates, causes no damage, e.g., rape and other cabbage varieties, sugar and fodder beets, and flax.

The agents according to the invention may be applied before or after emergence of the crop plants and unwanted plants. The preferred mode is after emergence of the unwanted plants.

The herbicidal agents according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient mixture as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The formulations contain from 0.1 to 95, and preferably 0.5 to 90, % by weight of active ingredient mixture. Examples of formulations are given below.

I. 20 parts by weight of a mixture of 4 parts by weight of 2-(1-ethoxyaminobutylidene)-5-(2-ethylthiopropyl)-cyclohexane-1,3-dione and 1 part by weight of the monoethanolammonium salt of 3,6-dichloro-2-picolinic acid is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient mixture.

II. 20 parts by weight of a mixture of 1 part by weight of 2-(1-ethoxyaminobutylidene)-5-(2-ethylthiopropyl)-cyclohexane-1,3-dione and 3 parts by weight of 3,6-dichloro-2-picolinic acid methyl ester is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient mixture.

III. 3 parts by weight of a mixture of 1 part by weight of 2-(1-allyloxyaminobutylidene)-5,5-dimethyl-4-methoxycarbonylcyclohexane-1,3-dione and 5 parts by weight of 3,5-dichloro-2-picolinic acid is intimately mixed with 97 parts by weight of particulate kaolin. A dust is obtained containing 3% by weight of the active ingredient mixture.

IV. 20 parts by weight of a mixture of 50 parts by weight of the sodium salt of 2-(1-allyloxyaminobutylidene)-5,5-dimethyl-4-methoxycarbonylcyclohexane-1,3-dione and 3 parts by weight of the sodium salt of 3,6-dichloro-2-picolinic acid is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 30 parts by weight of a mixture of 10 parts by weight of 2-(1-allyloxyaminobutylidene)-5,5-dimethylcyclohexane-1,3-dione and 1 part by weight of 3,6-dichloro-2-picolinic acid is intimately mixed with a mixture consisting of 92 parts by weight of powdered silica gel and 8 parts by weight of paraffin oil which has been sprayed onto the surface of this silica gel. A formulation of the active ingredient mixture is obtained having good adherence.

To increase the spectrum of action and to achieve further synergistic effects, the herbicidal agents according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenyl-carbamates, thiolcarbamates, halocarboxylic acids, triazines, amides, ureas, diphenyl ethers, triazinones, uracils, benzofuran derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
4,5-dimethoxy-2-(3-α,α,β-trifluoro-β-bromoethoxyphenyl)-3-(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichloroallyl)-(2,2,4-trimethylazetidine)-1-carbothiolate
S-(2,3,3-trichlorallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-(4'-trifluoromethylphenoxy)-pentene-2-carboxylate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide 2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy)-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
N-4-methyl-5-(trifluoromethyl)-sulfonylaminophenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yl-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitrophenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitrophenyl ether
2-chloro-4-trifluoromethylphenyl-3'-(2-fluoroethoxy)-4'-nitrophenyl ether
2-chloro-4-trifluoromethylphenyl-3'-ethoxycarbonylmethylthio-4'-nitrophenyl ether
2-chloro-4-trifluoromethyl-3'-methoxycarbonyl-4'-nitrophenyl ether
2,4,6-trichlorophenyl-3-ethoxycarbonylmethylthio-4'-nitrophenyl ether
2,4-dichlorophenyl-3'-methoxycarbonyl-4'-nitrophenyl ether
2,4-dichlorophenyl-3'-carboxy-4'-nitrophenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea 1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
1-acetyl-3-anilino-4-methoxycarbonyl-5-methylpyrazole
3-anilino-4-methoxycarbonyl-5-methylpyrazole
3-tert.-butylamino-4-methoxycarbonyl-5-methylpyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
methyl 2-[4-(4'-chlorophenoxymethyl)-phenoxy]-propionate
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
sodium chlorate
ammonium thiocyanate
calcium cyanamide.

It may also be useful to apply the mixtures according to the invention, either alone or together with other herbicides, in admixture with other crop protection agents, e.g., agents for combating pests or phytopathogenic fungi or bacteria. The compounds may also be mixed with solutions of mineral matters used to remedy nutritional or trace element deficiencies. To initiate the herbicidal action, wetting agents, spreader-stickers and non-phytotoxic oils and oil concentrates may be added.

Greenhouse experiments and experiments in the open demonstrate the synergistic increase in action achieved by the combined use of substituted cyclohexane-1,3-dione derivatives of the formula I and 3,6-dichloro-2-picolinic acid derivatives of the formula II in the herbicidal agents according to the invention.

The following active ingredients were employed: 2-(1-ethoxyaminobutylidene)-5-(2-ethylthiopropyl)-cyclohexane-1,3-dione (active ingredient A) and the monoethanolammonium salt of 3,6-dichloro-2-picolinic acid (active ingredient B).

For the greenhouse experiments, the vessels employed were plastic flowerpots having a volume of 300 cm³, and which were filled with a sandy loam containing about 1.5% humus. The seeds of the test plants were sown shallow, and separately, according to species. For the postemergence treatment, the plants were first grown in the vessels to a height of from 3 to 10 cm, depending on growth form, before being treated. The active ingredients and active ingredient mixtures were then applied, for instance at a rate of 0.03 kg/ha. The active ingredients were suspended, emulsified or dissolved in water and sprayed through finely distributing nozzles.

The experiments in the open were run on small plots. The results given in Tables 2 and 3 are average values from these experiments.

In the experiments in the open according to Table 2, the active ingredients or active ingredient mixtures were applied, in 750 liters of water per hectare as distributing medium, to *Echinochloa crus-galli* in the 3- to 5-leaf stage.

In the experiments in the open according to Table 3, the active ingredients or active ingredient mixtures were applied in 100 liters of water per hectare as distributing medium. In addition, a surfactant (Atplus 411 F+) was added which is made up essentially of polyethylene oxide sorbate and the mineral oil Sun Oil 11D, a commercial product of the Sun Oil company. The grasses were treated when 3 to 5 leaves (on average) had developed.

+trademark of Atlas Chemical Industries, Inc.

The damage to the plants was assessed on a 0 to 100 scale, 0 denoting no damage and normal growth, and 100 denoting complete destruction of at least the visible plant parts.

The experiments show that the herbicidal effectiveness of active ingredient A is surprisingly increased by being applied together with active ingredient B, which, at a rate of 0.3 kg/ha, has no effect on grass species. For instance, if (in the open) the ineffective amount of 0.3 kg/ha of active ingredient B is added to 0.15 kg/ha of active ingredient A, which causes slight damage to plants, grass species are damaged to an unexpectedly high extent (Table 2). The same is true when 0.06 kg/ha of active ingredient A is mixed with 0.06 kg/ha of B, or when 0.125 kg/ha of A is mixed with the same amount of B (Table 1). Just as surprising an effect is obtained when the small amount of 0.03 kg/ha of A is applied together with the same amount of B. The crop plants sugarbeets and rape are hardly damaged, if at all (Table 3).

The following plants were employed in the experiments: wild oats (*Avena fatua*), sugarbeets (*Beta vulgaris*), rape (*Brassica napus*), barnyardgrass (*Echinochloa crus-galli*), barley (voluntary; *Hordeum vulgare*), and wheat (voluntary; *Triticum aestivum*).

TABLE 1

Synergistic herbicidal action of the agents according to the invention; postemergence application in the open

| Active ingredient | Appln. rate [kg/ha] | % damage to Echinochloa crus-galli |
|---|---|---|
| A | 0.06 | 65 |
|   | 0.125 | 80 |
| B | 0.06 | 0 |
|   | 0.125 | 0 |
| A + B | 0.06 + 0.06 | 95 |
|   | 0.125 + 0.125 | 100 |

TABLE 2

Herbicidal action of the agents according to the invention on grassy species; postemergence application in the open

| Active ingredient+ | Appln. rate [kg/ha] | Voluntary barley | Voluntary wheat | Wild oats |
|---|---|---|---|---|
| A | 0.15 | 31 | 34 | 38 |
|   | 0.25 | 74 | 80 | 72 |
| B | 0.3 | 0 | 0 | 0 |
| A + B | 0.15 + 0.3 | 78 | 76 | 74 |
|   | 0.25 + 0.3 | 88 | 94 | 88 |

0 = no damage, 100 = plants destroyed
+All treatments in this table additionally contained 0.5 l/ha of Atplus 411 F

TABLE 3

Selective control of wild oats in crops with the herbicidal mixtures according to the invention; postemergence application in the greenhouse

| Active ingredient | Appln. rate [kg/ha] | Beta vulgaris | Brassica napus | Avena fatua |
|---|---|---|---|---|
| A | 0.03 | 0 | 0 | 65 |
| B | 0.03 | 0 | 0 | 5 |
| A + B | 0.03 + 0.03 | 5 | 0 | 80 |

We claim:

1. A herbicidal agent consisting essentially of a mixture of 2-(1-ethoxyaminobutylidene)-5-(2-ethylthiopropyl)-cyclohexane-1,3-diione (I) or a metal salt, an unsubstituted or substituted ammonium salt, or a hydrate of said compound and a 3,6-dichloro-2-picolinic acid derivative of the formula II

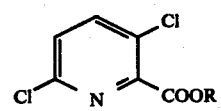

where R is hydrogen or straight-chain or branched alkyl of 1 to 4 carbon atoms, or a metal salt or unsubstituted or substituted ammonium salt of the acid, wherein the ratio of compound (I) to compound (II) is from 1:0.06 to 1:5.

2. A herbicidal agent consisting essentially of a mixture of 2-(1-ethoxyaminobutylidene)-5-(2-ethylthiopropyl)-cyclohexane-1,3-dione or a metal salt, an unsubstituted or substituted ammonium salt or a hydrate thereof and 3,6-dichloro-2-picolinic acid or a metal salt or an unsubstituted or substituted ammonium salt thereof, wherein the ratio of the cyclohexane-1,3-dione derivative to the picolinic acid derivative is from 1:5 to 1:0.025.

* * * * *